(12) United States Patent
Babiner

(10) Patent No.: US 9,498,305 B2
(45) Date of Patent: Nov. 22, 2016

(54) ENDOSSEOUS DENTAL IMPLANT AND ABUTMENT FOR PREVENTION OF BONE LOSS

(71) Applicant: Boris D. S. Babiner, Philadelphia, PA (US)

(72) Inventor: Boris D. S. Babiner, Philadelphia, PA (US)

( * ) Notice: Subject to any disclaimer, the term of this patent is extended or adjusted under 35 U.S.C. 154(b) by 0 days.

(21) Appl. No.: 14/182,948

(22) Filed: Feb. 18, 2014

(65) Prior Publication Data

US 2014/0242546 A1    Aug. 28, 2014

Related U.S. Application Data

(60) Provisional application No. 61/767,958, filed on Feb. 22, 2013.

(51) Int. Cl.
*A61C 13/12*    (2006.01)
*A61C 8/00*    (2006.01)

(52) U.S. Cl.
CPC ........... *A61C 8/0025* (2013.01); *A61C 8/0069* (2013.01)

(58) Field of Classification Search
CPC .... A61C 8/00; A61C 8/0001; A61C 8/0003; A61C 8/0004; A61C 8/0006; A61C 8/001; A61C 8/0019; A61C 8/0025; A61C 8/003; A61C 8/0031; A61C 8/0033; A61C 8/0034; A61C 8/0037; A61C 8/0045; A61C 8/0046; A61C 8/0051; A61C 8/0063; A61C 8/0065; A61C 8/0066; A61C 8/0069; A61C 8/0072
USPC .................................................. 433/172–176
See application file for complete search history.

(56) References Cited

U.S. PATENT DOCUMENTS

| 2,402,342 | A | * | 6/1946 | Phillips | ............... F16B 23/0023 411/404 |
| 4,202,244 | A | * | 5/1980 | Gutshall | ............. F16B 23/0023 411/404 |
| 4,344,757 | A | | 8/1982 | Streel | |

(Continued)

FOREIGN PATENT DOCUMENTS

| WO | 2005065571 | 7/2005 |
| WO | 2012143475 | 10/2012 |

(Continued)

OTHER PUBLICATIONS

Paragon (Core-Vent) Sulzer Dental (2002).

(Continued)

*Primary Examiner* — Yogesh Patel
(74) *Attorney, Agent, or Firm* — Niels Haun; Dann, Dorfman, Herrell and Skillman, P.C.

(57) ABSTRACT

Endosseous dental implants and abutments for deterring tissue loss, such as loss of buccal bone, at the site of the implant/abutment. An exemplary implant may include longitudinally extending externally threaded and unthreaded regions each extending over only a circumferential portion of the external circumference of the implant. The implant may include an internal passage extending along the shaft having a frusto-conical region extending over only a circumferential portion of the internal passage. An exemplary abutment may include a distal connection end comprising a frusto-conical region thereat extending over only a circumferential portion of the external circumference of the connection end to provide a frusto-conical connection region and non-frusto-conical connection region.

26 Claims, 4 Drawing Sheets

(56) References Cited

U.S. PATENT DOCUMENTS

| | | | |
|---|---|---|---|
| 4,713,003 A * | 12/1987 | Symington et al. | 433/173 |
| 5,009,596 A * | 4/1991 | Soderberg | 433/173 |
| 5,076,788 A * | 12/1991 | Niznick | A61C 8/0018 |
| | | | 433/173 |
| 5,312,256 A * | 5/1994 | Scortecci | 433/174 |
| 5,695,336 A | 12/1997 | Lazzara | |
| 5,810,590 A | 9/1998 | Fried | |
| 5,927,979 A * | 7/1999 | Misch | A61C 8/0022 |
| | | | 433/172 |
| 6,126,445 A | 10/2000 | Willoughby | |
| 6,174,167 B1 | 1/2001 | Wohrle | |
| 6,283,754 B1 | 9/2001 | Wohrle | |
| 6,379,153 B1 * | 4/2002 | Schroering | A61C 8/0018 |
| | | | 433/173 |
| 6,663,388 B1 | 12/2003 | Schar | |
| 6,726,481 B1 * | 4/2004 | Zickmann et al. | 433/173 |
| 7,238,186 B2 * | 7/2007 | Zdeblick et al. | 623/17.16 |
| 7,396,231 B2 | 7/2008 | Niznick | |
| 7,677,891 B2 | 3/2010 | Niznick | |
| 7,699,613 B2 | 4/2010 | Niznick | |
| 7,785,107 B2 | 8/2010 | Niznick | |
| RE42,391 E | 5/2011 | Wohrle | |
| 8,118,596 B2 | 2/2012 | Niznick | |
| 2002/0102518 A1 | 8/2002 | Mena | |
| 2003/0082498 A1* | 5/2003 | Halldin et al. | 433/173 |
| 2006/0147880 A1* | 7/2006 | Krumsiek et al. | 433/174 |
| 2006/0154205 A1 | 7/2006 | Reggie | |
| 2006/0246399 A1 | 11/2006 | Ehrl | |
| 2007/0037123 A1 | 2/2007 | Mansueto | |
| 2008/0299516 A1 | 12/2008 | Aldecoa | |
| 2011/0189633 A1* | 8/2011 | Schneck | A61C 8/0022 |
| | | | 433/174 |
| 2012/0270179 A1 | 10/2012 | Holmstrom et al. | |
| 2012/0288826 A1* | 11/2012 | Fitton, III | A61C 8/0068 |
| | | | 433/174 |
| 2014/0134570 A1* | 5/2014 | Zipprich | A61C 8/005 |
| | | | 433/173 |

FOREIGN PATENT DOCUMENTS

| | | |
|---|---|---|
| WO | 2012164560 | 12/2012 |
| WO | 2013083125 | 6/2013 |

OTHER PUBLICATIONS

International Search Report in related International Application No. PCT/US2014/016862, dated Jul. 1, 2014.
Written Opinion of the International Searching Authority in related International Application No. PCT/US2014/016862, dated Jul. 1, 2014.
"Handling Procedures for ATLANTIS abutment, zirconia," 2012.
Meleo, et al., "Fixture-abutment connection surface and micro-gap measurements by 3D micro-tomographic technique analysis," Ann 1st Super Sanita (2012) 48:53-58.
Zubery, et al., "Bone Resorption Caused by Three Periodontal Pathogens In Vivo in Mice is Mediated in Part by Prostaglandin," Infection and Immunity (1998) 66:4158-4162.
Albrektsson, et al., "Failure of Core-Vent Implants: A Retrieval Analysis of 19 Hollow Basket Implants," Clinical Materials (1992) 10:219-224.
"A Sophisticated Connection for Exceptional Mechanical Stability and Reliability," Thommen Medical, http://www.thommenmedical.com/en/experts/thommen-implant-system/ connection.html, dated Oct. 28, 2012.
Nobel Perfect Groovy, Procedures & Products, Nobel Biocare, 2005.
Boakaya, D., et al., "Mechanics of the Tapered Interference Fit in Dental Implants", Journal of Biomechanics, Oct. 2002.
Baxie, S., et al., "Microgap Between Zirconia Abutments and Titanium Implants", The International Journal of Oral & Maxillofacial Implants, vol. 25, No. 3, 2010, pp. 456-460.
Harder, S., et al., "Molecular Leakage at Implant-Abutment Connection—In Vitro Investigation of Tightness of Internal Conical Implant-Abutment Connections Against Endotoxin Penetration", Clin Oral Invest, 2010, pp. 427-432.
Jansen, V., et al., "Microbial Leakage and Marginal Fit of the Implant-Abutment Interface", JOMI, 1997, vol. 12, No. 4, pp. 527-540.
Boakaya, D., et al., "Efficiency Considerations for the Purely Tapered Interference Fit (TIF) Abutments Used in Dental Implants", Journal of Biomedical Engineering, Aug. 2004, vol. 126, pp. 393-401.
Zimmer Dental, "Internal Hex with Friction Fit", © 2005 Zimmer Dental Inc., 6 pages.
Supplementary European search report from EP Application No. 14754144.5 Sep. 2, 2016.

* cited by examiner

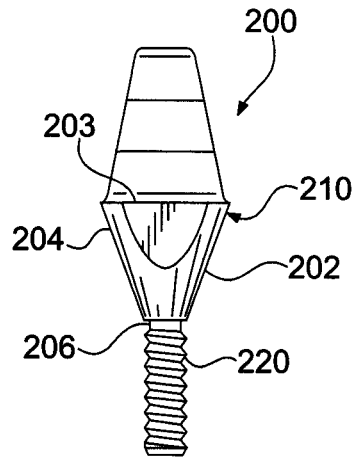
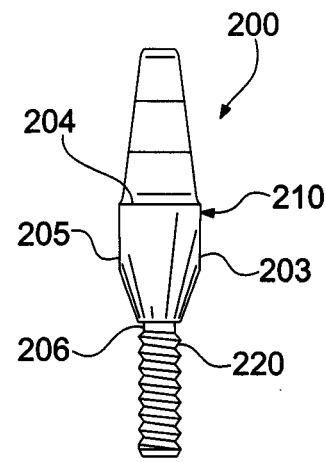
FIG. 3A                FIG. 3B
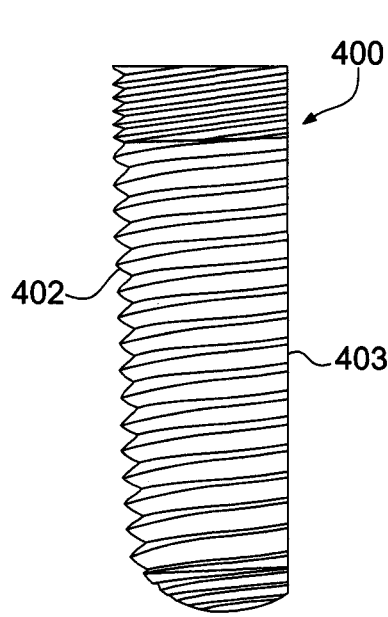
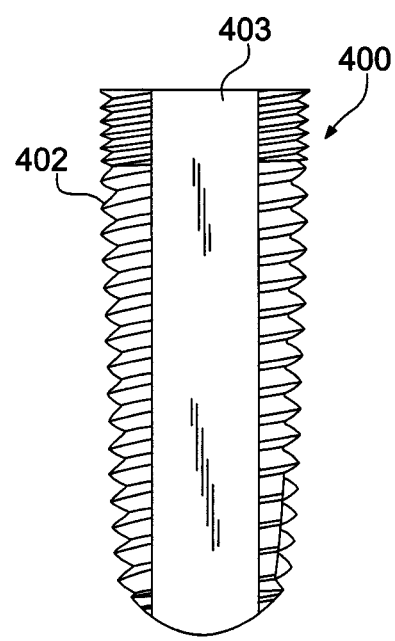
FIG. 4A                FIG. 4B

US 9,498,305 B2

ENDOSSEOUS DENTAL IMPLANT AND ABUTMENT FOR PREVENTION OF BONE LOSS

RELATED APPLICATIONS

This application claims the benefit of priority of U.S. Provisional Application No. 61/767,958, filed on Feb. 22, 2013, the entire contents of which application are incorporated herein by reference.

FIELD OF THE INVENTION

The present invention relates generally to endosseous dental implants and abutments, and more particularly, but not exclusively, to, endosseous dental implants and abutments for deterring tissue loss, such as loss of buccal bone, at the site of the implant/abutment.

BACKGROUND OF THE INVENTION

A dental implant is a device used to anchor, via an abutment, a dental prosthesis into living bone and tissue. The implant is placed into bone tissue to provide a solid foundation for the abutment and prosthesis attached to the abutment. Dental implants, abutments, and their prostheses serve numerous purposes, such as: chewing, where they oppose teeth or other prosthesis to allow mastication to take place; preventing extrusion of opposing teeth by providing sensory input and contact; and, providing an aesthetic appearance.

In order to place an implant into the jawbone, the recipient site in the jawbone typically needs to be shaped with drills or other tools, such as expanders and piezoelectric tips, to prepare the site for implant placement. Dental implants may be placed immediately after extraction or after healing of the extraction site with or without a grafting material. Frequently, it may be difficult to achieve the required thickness of buccal bone with an implant of adequate width to provide sufficient support for the prosthesis. In such a case, a lack of sufficient buccal bone may result in the loss of supporting tissues (bone and gums) due to a reduced surface area of blood supply around the implant. Lack of sufficient buccal bone presents a dilemma for the clinician, because use of an narrower implant and abutment that may better fit within the buccal bone may experience failure during use due to overloading with bite forces whereas use of a wider implant (and accompanying abutment) may compromise aesthetics and result in potential tissue loss sequelae.

Accordingly, it would be an advance in the art to provide dental implants and abutments that overcome the problems associated with potential bone and/or gum tissue loss sequelae, while providing sufficient prosthesis support and preserving aesthetics.

SUMMARY OF THE INVENTION

As an advance to the field of dental implants, implants and abutments in accordance with the present invention are provided which are structured to provide sufficient support for a dental prosthesis attached thereto, while at the same time allowing for sufficient bone tissue around the implant to prevent negative outcomes, such as bone tissue loss. In this regard, in one of its aspects the present invention provides a dental implant and abutments having a first width, in a first direction transverse to the longitudinal axis of the implant, which is sufficiently large to provide support for the dental prosthesis. The outer circumference of the dental implant on opposing sides across the first width may be externally threaded for insertion into the jawbone of a patient. The dental implant may have a second width, in a second transverse direction perpendicular to the first transverse direction, which is smaller than the first width. This smaller second width may be oriented in the patient's jawbone to provide additional bone mass adjacent the implant surfaces disposed on opposing sides across the second width. However, the presence of the smaller second width of the implant may require the use novel abutments that account for the smaller second width while providing the requisite support for a dental prosthesis attached thereto. In this regard, the present invention provides a dental implant abutment comprising a connection region designed to maintain mechanical integrity having a first width and a relatively smaller second width each width corresponding the to the first and second widths of the implant. The connection region may be provided the form of one or more conical taper portions with one or more flat connecting wall(s), for instance. Thus, dental implants and abutments in accordance with the present invention may be structured to have differing transverse widths, where the relatively larger width provides the required support and the relatively smaller width enables an increased thickness of bone tissue proximate the implant surfaces defining the relatively smaller width.

For example, in one of its aspects the present invention provides an endosseous dental implant for insertion into the jawbone of a patient having a configuration for deterring bone loss at the site of the implant. In one exemplary configuration, the implant may include a longitudinally extending shaft having a longitudinal axis extending from a proximal abutment end to a distal end; the shaft may have an external circumference perpendicular to the longitudinal axis associated therewith. A first longitudinally extending externally threaded region may be provided extending along the longitudinal axis and extending over only a circumferential portion of the external circumference of the shaft. A first longitudinally extending unthreaded region may be provided extending over only a circumferential portion of the external circumference of the shaft at a location longitudinally adjacent to the first longitudinally extending externally threaded region. An internal passage may extend along the longitudinal axis of the shaft from the proximal abutment end of the shaft and may include a frusto-conical region extending over only a circumferential portion of the internal passage proximate the abutment end of the shaft to provide a frusto-conical connection region and non-frusto-conical connection region. The internal passage may include a truncated circular cross-sectional shape in a plane perpendicular to the longitudinal axis proximate the abutment end of the shaft and may include a frusto-conical region extending over only a circumferential portion of the internal passage proximate the abutment end of the shaft. The internal passage may also include first and second frusto-conical regions extending over only a circumferential portion of the internal passage proximate the abutment end of the shaft, with the first and second frusto-conical regions disposed at opposing circumferential locations of the internal passage. First and second planar surfaces may be disposed between the first and second frusto-conical regions, respectively.

In addition, a second longitudinally extending externally threaded region may be provided extending along the longitudinal axis and extending over only a circumferential portion of the external circumference of the shaft, wherein the first and second longitudinally extending externally threaded regions may be disposed at opposing locations across the longitudinal axis about the external circumference of the shaft. The implant may also include a second longitudinally extending unthreaded region extending along the longitudinal axis and extending over only a circumferential portion of the external circumference of the shaft. The first and second longitudinally extending unthreaded regions may be disposed between the first and second longitudinally extending externally threaded regions at opposing locations across the longitudinal axis about the external circumference of the shaft. The first and second longitudinally extending externally threaded regions may be disposed a first distance apart as measured along a first diameter in a plane perpendicular to the longitudinal axis, and the first and second longitudinally extending unthreaded regions may be disposed a second distance apart as measured along a second diameter in the plane, wherein the second distance is less than the first distance. In an exemplary configuration, the first and second longitudinally extending unthreaded regions may include substantially flat planar regions. Selected surfaces, such as the first and second longitudinally extending unthreaded regions and/or threaded regions may be textured to promote bone growth therein.

In another of its aspects, the present invention may provide a dental implant abutment for insertion into a dental implant. The dental implant abutment may include a longitudinally extending shaft having a longitudinal axis and an external circumference perpendicular to the axis associated therewith. In an exemplary configuration, the abutment may include a distal connection end comprising a first frusto-conical region thereat extending over only a circumferential portion of the external circumference of the connection end to provide a frusto-conical connection region and non-frusto-conical connection region. The non-frusto-conical connection region may include a planar surface parallel to the longitudinal axis or tilted relative to the longitudinal axis. A second frusto-conical region may be provided extending over only a circumferential portion of the external circumference of the connection end, and the first and second frusto-conical regions may be disposed at opposing circumferential locations of the external circumference. Additionally, first and second planar surfaces may be disposed between the first and second frusto-conical regions at opposing circumferential locations of the external circumference, respectively.

BRIEF DESCRIPTION OF THE DRAWINGS

The foregoing summary and the following detailed description of exemplary embodiments of the present invention may be further understood when read in conjunction with the appended drawings, in which:

FIGS. 3A, 3B schematically illustrate side views of an exemplary dental implant abutment in accordance with the present invention having first and second frusto-conical regions disposed at opposing circumferential locations at a connection portion of the abutment and having two planar surfaces disposed between the first and second frusto-conical regions, respectively;

FIGS. 4A, 4B schematically illustrate side views of an exemplary dental implant in accordance with the present invention having one longitudinally extending threaded region and one longitudinally extending unthreaded region adjacent thereto.

DETAILED DESCRIPTION OF THE INVENTION

Figure 1A:
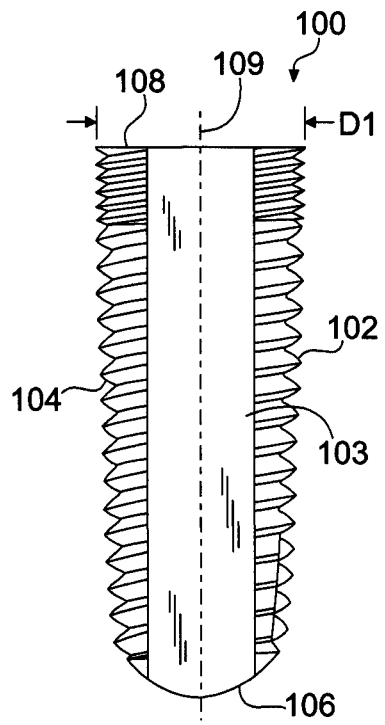
FIGS. 1A, 1B schematically illustrate side views of an exemplary dental implant in accordance with the present invention having two longitudinally extending threaded regions disposed at opposing locations across a longitudinal axis of the shaft and two longitudinally extending unthreaded regions disposed therebetween.

Referring now to the figures, wherein like elements are numbered alike throughout, FIGS. 1A-1E schematically illustrate in exemplary configuration of an endosseous dental implant 100 in accordance with the present invention which is structured to deter or prevent tissue loss in a patient at the site of implantation. In this regard, the endosseous dental implant 100 may have a diameter D1 in a first selected direction perpendicular to the longitudinal axis 109 of the implant 100 and a relatively smaller diameter D2 in a second direction orthogonal to the first selected direction. Such a configuration has the benefit of providing increased implant stability in view of the relatively larger diameter D1 and decreased chance of tissue loss in view of the relatively smaller diameter D2 by providing increased clearance between selected surfaces 103, 105 of the implant 100 and the buccal and lingual surfaces 11, 13 of the bone tissue 10 into which the implant 100 is inserted, for example, FIG. 2A. The presence of additional bone tissue between the implant 100 and the buccal and lingual surfaces 11, 13 can prevent or deter bone resorption and loss.

Figure 1B:
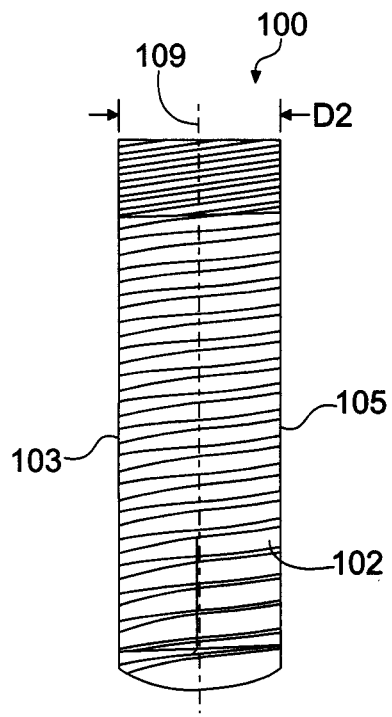
Figure 1C:
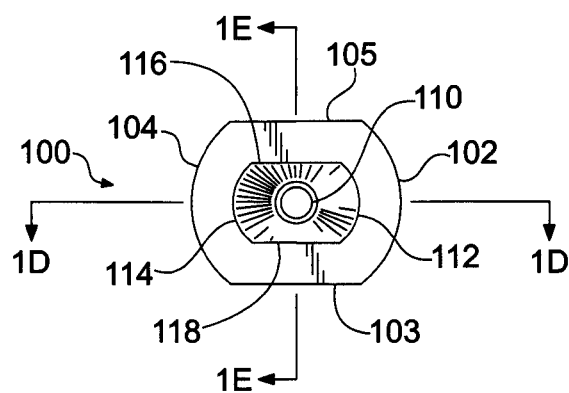
FIG. 1C schematically illustrates a top-view of the dental implant of FIGS. 1A, 1B.
Figure 1D:
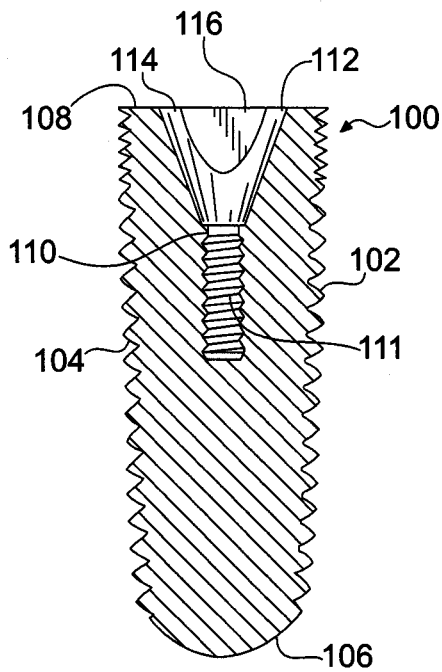
FIGS. 1D, 1E schematically illustrate cross-sectional views of the dental implant of FIGS. 1A, 1B showing the internal passageway for receiving a dental implant abutment.
Figure 1E:
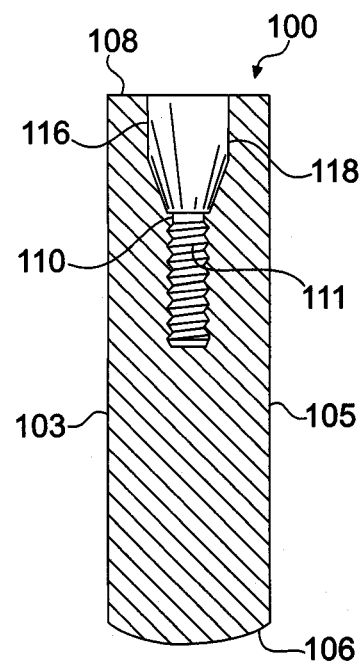

Turning to the structure of the endosseous dental implant 100 more specifically, FIGS. 1A, 1B schematically illustrate side views taken from two orthogonal directions of an exemplary configuration of the endosseous dental implant 100 in accordance with the present invention having first and second longitudinally extending externally threaded regions 102, 104 and first and second longitudinally extending unthreaded regions 103, 105, which may comprise planar or other suitably shaped surfaces. The longitudinally extending externally threaded regions 102, 104 may extend over only a circumferential portion of the external circumference of the implant 100 and may be disposed at opposing locations across the longitudinal axis 109, FIGS. 1A, 1C. Likewise, the longitudinally extending unthreaded regions 103, 105 may extend over only a circumferential portion of the external circumference of the implant 100 and may be disposed at opposing locations across the longitudinal axis 109, FIGS. 1B, 1C. The longitudinally extending externally threaded and unthreaded regions 102, 104, 103, 105 may be longitudinally adjacent to one another, such that at a cross-section perpendicular to the longitudinal axis 109 there are two opposing threaded regions 102, 104 with two opposing unthreaded regions 103, 105 disposed therebetween, FIGS. 1A-1C. Thus, a first diameter D1 may be defined as extending in a plane perpendicular to the longitudinal axis 109 between the first and second longitudinally extending threaded regions 102, 104. Similarly, a second diameter D2 may be defined as extending in the same perpendicular plane between the first and second longitudinally extending unthreaded regions 103, 105. The first diameter D1 may have a value of 4.3 mm, 4.8 mm, or 5.8 mm, and the second diameter D2 may have a diameter of 3.3 mm, for example. In addition, the endosseous dental implant 100 may be tapered from a proximal abutment end 108 to a distal end 106 in a plane containing the longitudinal axis 109 and intersecting the first and second longitudinally extending externally threaded regions 102, 104, FIG. 1A. Conversely, the longitudinally extending unthreaded regions 103, 105 may be parallel to one another to provide a non-tapered cross-section of the endosseous dental implant 100, FIG. 1B. The cross-section may take the form of a truncated circle, FIG. 1C; as used herein the term "truncated circle" refers to a circle having at least one chord which truncates the circle, such as the truncated circle illustrated in FIG. 1C having two opposing chords to provide a doubly truncated circular cross-section, for example. Independent of the particular shape of the implant 100, any of the longitudinally extending regions 102, 103, 104, 105 or other portions of the implant 100 for insertion into bone tissue may be roughened or textured to encourage bone growth therein. Any suitable process may be used to achieve the roughening or texture, such as a removal process, e.g., acid etching or particle blasting, or an additive process, e.g., deposition of hydroxyapatite, a protein, or growth factor, for example. In addition, the implant 100 itself may comprise any suitable material, such as titanium or a titanium alloy, for example.

While the exemplary endosseous dental implant 100 of FIGS. 1A-1E are shown with two threaded regions 102, 104 and two unthreaded regions 103, 105, other configurations are possible. For example, with reference to FIGS. 4A, 4B, an endosseous dental implant 400 may include a single longitudinally extending externally threaded region 402 and a single longitudinally extending unthreaded region 403, each extending over only a circumferential portion of the external circumference.

Figure 2A:
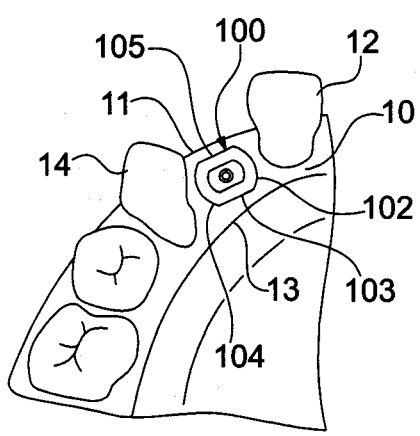
FIGS. 2A, 2B schematically illustrate top-views of the dental implant of FIGS. 1A, 1B disposed in situ in a patient's jawbone at differing orientations.
Figure 2B:
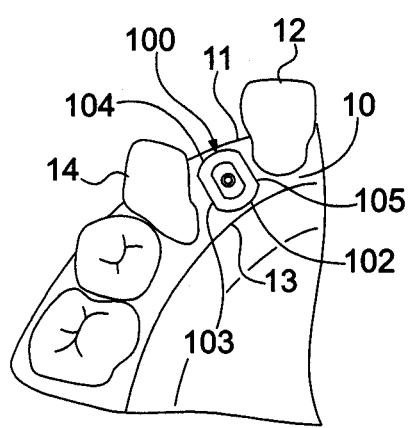

In one exemplary use, the implant 100 may be oriented in the jawbone 10 of a patient such that the longitudinally extending unthreaded regions 103, 105 are disposed generally parallel to the buccal and lingual surfaces 11, 13 of the jawbone 10 to provide additional space for the bone tissue between the longitudinally extending unthreaded regions 103, 105 and the buccal and lingual surfaces 11, 13, FIG. 2A. Such an orientation is expected to deter bone loss and promote implant support due to the presence of additional bone tissue between the buccal and/or lingual surfaces 11, 13 and the implant 100. In a further exemplary use, the implant 100 may be oriented in the jawbone 10 such that the longitudinally extending externally threaded regions 102, 104 are disposed proximate the buccal and lingual surfaces 11, 13, so that the longitudinally extending unthreaded regions 103, 105 are disposed proximate adjacent teeth 12, 14 to provide additional space between the implant 100 and the teeth 12, 14, FIG. 2B. This orientation may be desirable where the distance between the teeth 12, 14 is particularly narrow, and is expected to prevent bone loss as well as destabilization of the implant and damage to the roots of the adjacent teeth 12, 14. For example, such orientation may provide distance of 1.5 mm between the implant 100 and each tooth 12, 14 to allow dental papilla formation.

The endosseous dental implant 100 may further include an internal passage 110 for receiving an abutment 200 to which a dental prosthesis may be attached, FIGS. 1D, 1E, 3A, 3B. The internal passage 110 may include an internally threaded portion 111 for receiving a screw 220 to attach the abutment 200 to the implant 100. In this regard, the abutment 200 may include a longitudinally extending passage therethrough for receiving the screw 220. The internal passage 110 may include first and second frusto-conical regions 112, 114 extending over only a circumferential portion of the internal passage 110 proximate the abutment end 108 of the implant 110, and may include first and second planar surfaces 116, 118 extending over only a circumferential portion of the internal passage 110 between the first and second frusto-conical regions 112, 114, respectively, FIGS. 1D, 1E.

Figure 5:
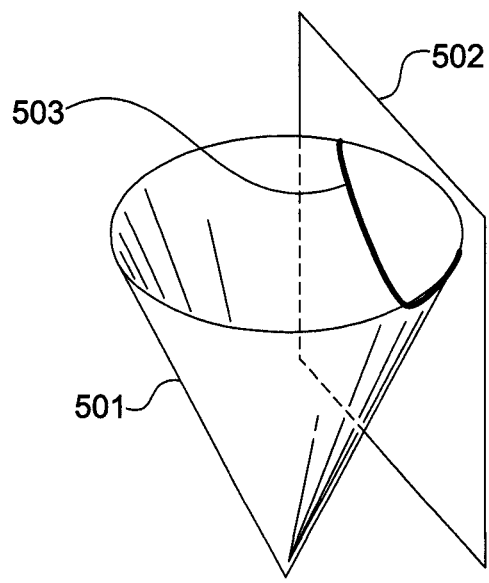
FIG. 5 schematically illustrates a conic section formed by the intersection of a cone with a plane.

A connection 210 may be provided at the connection end 206 of the abutment 200 and may be shaped to be indexed to the shape of the frusto-conical regions 112, 114 and planar surfaces 116, 118 of the internal passage 110 of the implant 100, FIGS. 3A, 3B. For example, the connection 210 may include first and second frusto-conical regions 202, 204 extending over only a circumferential portion of the external circumference of the connection 210 and disposed at opposing circumferential locations to provide frusto-conical connection regions 202, 204 and non-frusto-conical connection regions 203, 205, which are indexed to the frusto-conical regions 112, 114 and planar surfaces 116, 118 of the implant 100, respectively. The planar surfaces 116, 118 may be provided in the form bounded by a conic section, such as formed by a cone 501 intersected by a plane 502 parallel to the cone axis, FIG. 5, in which case the conic section boundary between planar and conic surfaces is a hyperbola 503. Thus, the boundary between the frusto-conical connection regions 202, 204 and non-frusto-conical connection regions 203, 205 may be in the form of a hyperbola. The frusto-conical connection regions 202, 204 may have a shape similar to a Morse taper, and the non-frusto-conical connection regions 203, 205 may be provided in the form of planar surfaces that are parallel to a longitudinal axis of the abutment 200. However, the planar surfaces 116, 118 may be tilted relative to the longitudinal axis of the abutment 200. The frusto-conical connection regions 202, 204 may permit platform switching/shifting that enables interdental papilla preservation by moving a potential microgap between the implant 100 and abutment 200, allowing better blood supply at the bone and connective tissue interface, thus maximizing the aesthetic outcome.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

What is claimed is:

1. An endosseous dental implant for insertion into the jawbone of a patient and deterring bone loss at the site of the implant, comprising:
    a longitudinally extending shaft having a longitudinal axis extending from a proximal abutment end to a distal end, and having an external circumference perpendicular to the longitudinal axis associated therewith;
    a first longitudinally extending externally threaded region extending along the longitudinal axis and extending over only a circumferential portion of the external circumference of the shaft;

a first longitudinally extending unthreaded region extending over only a circumferential portion of the external circumference of the shaft at a location longitudinally adjacent to the first longitudinally extending externally threaded region; and an internal passage extending along the longitudinal axis of the shaft from the proximal abutment end of the shaft, the internal passage comprising first and second frusto-conical regions each extending over only a circumferential portion of the internal passage proximate the abutment end of the shaft to provide a frusto-conical region at opposing circumferential locations of the internal passage, and a non-frusto-conical region disposed between the first and second frusto-conical regions, wherein the first frusto-conical region is disposed adjacent the longitudinally extending externally threaded region and the non-frusto-conical region is disposed adjacent the longitudinally extending unthreaded region.

2. The endosseous dental implant according to claim 1, wherein the internal passage comprises a truncated circular cross-sectional shape in a plane perpendicular to the longitudinal axis proximate the abutment end of the shaft.

3. The endosseous dental implant according to claim 1, comprising first and second planar surfaces disposed between the first and second frusto-conical regions, respectively.

4. The endosseous dental implant according to claim 1, comprising a second longitudinally extending externally threaded region extending along the longitudinal axis and extending over only a circumferential portion of the external circumference of the shaft, the first and second longitudinally extending externally threaded regions disposed at opposing locations across the longitudinal axis about the external circumference of the shaft.

5. The endosseous dental implant according to claim 4, comprising a second longitudinally extending unthreaded region extending along the longitudinal axis and extending over only a circumferential portion of the external circumference of the shaft, the first and second longitudinally extending unthreaded regions disposed between the first and second longitudinally extending externally threaded regions at opposing locations across the longitudinal axis about the external circumference of the shaft.

6. The endosseous dental implant according to claim 5, wherein the first and second longitudinally extending externally threaded regions are disposed a first distance apart as measured along a first diameter in a plane perpendicular to the longitudinal axis, and wherein the first and second longitudinally extending unthreaded regions are disposed a second distance apart as measured along a second diameter in the plane, wherein the second distance is less than the first distance.

7. The endosseous dental implant according to claim 5, wherein the first and second longitudinally extending unthreaded regions comprise substantially flat planar regions.

8. The endosseous dental implant according to claim 5, wherein the first and second longitudinally extending unthreaded regions are textured to promote bone growth therein.

9. The endosseous dental implant according to claim 5, wherein the first and second longitudinally extending unthreaded regions are disposed at the proximal abutment end of the implant.

10. The endosseous dental implant according to claim 5, wherein the first and second longitudinally extending unthreaded regions extend along substantially the entire length of the implant.

11. The endosseous dental implant according to claim 1, wherein the shaft is tapered from a first end to a second end along the longitudinal axis in a plane containing the longitudinal axis and intersecting the first longitudinally extending externally threaded region.

12. The endosseous dental implant according to claim 1, wherein the shaft has a truncated circular cross-sectional shape in a plane perpendicular to the longitudinal axis.

13. The endosseous dental implant according to claim 1, wherein the first longitudinally extending externally threaded region is continuously threaded throughout the circumferential portion proximate the distal end.

14. The endosseous dental implant according to claim 1, wherein the internal passage comprises a threaded section extending from the frusto-conical region towards the distal end.

15. The endosseous dental implant according to claim 1, wherein the longitudinally extending shaft includes a solid exterior wall surrounding the internal passage and extending along the entire length of the internal passage to prevent communication between the internal passage the exterior of the shaft through the wall.

16. The endosseous dental implant according to claim 1, wherein the first longitudinally extending unthreaded region is disposed at the proximal abutment end of the implant.

17. The endosseous dental implant according to claim 1, wherein the first longitudinally extending unthreaded region extends along substantially the entire length of the implant.

18. The endosseous dental implant according to claim 1, wherein the non-frusto-conical region is disposed in a plane parallel to the first longitudinally extending unthreaded region.

19. A dental implant system comprising the implant of claim 1 and an abutment configured for insertion into the dental implant, the abutment comprising a longitudinally extending shaft having a longitudinal axis and an external circumference perpendicular to the axis associated therewith, and the abutment having a distal connection end comprising a first frusto-conical region thereat extending over only a circumferential portion of the external circumference of the connection end to provide a frusto-conical connection region and a non-frusto-conical connection region adjacent to the frusto-conical connection region.

20. The dental implant system according to claim 19, wherein the non-frusto-conical connection region comprises a planar surface parallel to the longitudinal axis.

21. The dental implant system according to claim 19, wherein the non-frusto-conical connection region comprises a planar surface tilted relative to the longitudinal axis.

22. The dental implant system according to claim 19, the abutment comprising a second frusto-conical region extending over only a circumferential portion of the external circumference of the connection end, the first and second frusto-conical regions disposed at opposing circumferential locations of the external circumference.

23. The dental implant system according to claim 22, the abutment comprising first and second planar surfaces disposed between the first and second frusto-conical regions at opposing circumferential locations of the external circumference, respectively.

24. The dental implant system according to claim 19, wherein the shaft of the abutment has a truncated circular cross-sectional shape in a plane perpendicular to the longitudinal axis.

25. The dental implant system according to claim 19, wherein the abutment comprises an internal passage extending along the longitudinal axis thereof for the entire length of the shaft.

26. The dental implant system according to claim 19, wherein the external circumference of the abutment is unthreaded.

* * * * *